(12) United States Patent
Di Puccio Pagano

(10) Patent No.: US 7,988,981 B2
(45) Date of Patent: Aug. 2, 2011

(54) MULTIPHASE COSMETIC COMPOSITION

(75) Inventor: Erica Luiza Di Puccio Pagano, Jardim Marajoara (BR)

(73) Assignee: Natura Cosmeticos S.A., Sao Paulo (BR)

( * ) Notice: Subject to any disclaimer, the term of this patent is extended or adjusted under 35 U.S.C. 154(b) by 1098 days.

(21) Appl. No.: 10/510,845

(22) PCT Filed: Apr. 14, 2003

(86) PCT No.: PCT/IB03/01390
§ 371 (c)(1),
(2), (4) Date: Jul. 11, 2005

(87) PCT Pub. No.: WO03/086330
PCT Pub. Date: Oct. 23, 2003

(65) Prior Publication Data
US 2005/0249758 A1    Nov. 10, 2005

(30) Foreign Application Priority Data

Apr. 12, 2002 (BR) ..................................... 0201235

(51) Int. Cl.
*A61K 8/02* (2006.01)
*A61K 8/03* (2006.01)
(52) U.S. Cl. ........................................ 424/401; 424/400
(58) Field of Classification Search ........................ None
See application file for complete search history.

(56) References Cited

U.S. PATENT DOCUMENTS

| 4,525,344 A | * | 6/1985 | Tutsky | 424/73 |
| 6,200,579 B1 | * | 3/2001 | Picard | 424/401 |
| 6,649,174 B2 | * | 11/2003 | Najdek et al. | 424/401 |
| 2002/0031478 A1 | | 3/2002 | Keller et al. | |

FOREIGN PATENT DOCUMENTS

| EP | 0 882 442 | | 12/1998 |
| EP | 0882442 A1 | * | 12/1998 |
| JP | 63033316 | | 2/1988 |
| JP | 63033317 | | 2/1988 |
| JP | 63083009 | | 4/1988 |
| JP | 63083010 | | 4/1988 |
| JP | 63083011 | | 4/1988 |
| JP | 63165304 | | 7/1988 |
| JP | 63165305 | | 7/1988 |
| JP | 1040413 | | 2/1989 |
| JP | 4290810 | | 10/1992 |

OTHER PUBLICATIONS

International Search Report for PCT/IB03/01390 completed Sep. 19, 2003.

* cited by examiner

*Primary Examiner* — Anand Desai
*Assistant Examiner* — Melissa Mercier
(74) *Attorney, Agent, or Firm* — Alston & Bird LLP

(57) ABSTRACT

The present invention relates to a multi-phase cosmetic composition for application to the body, which has a liquid and transparent appearance, becomes a homogeneous mixture after being stirred, the phases raps idly separating when at rest. The composition according to the present invention comprises at least one oily phase and at least one aqueous phase, further comprising a polyol, the oily phase comprising a mixture of at least one mineral oil and at least one vegetable oil, and the aqueous phase comprising a water-soluble salt.

11 Claims, No Drawings

MULTIPHASE COSMETIC COMPOSITION

FILED OF THE INVENTION

The present invention relates to a cosmetic composition consisting of two or more phases or layers, either colored or not, for application onto the body, and which has a liquid and transparent appearance, becomes a homogeneous mixture after being stirred, phases rapidly separating when at rest.

BACKGROUND OF THE INVENTION

Compositions for cosmetic use, more specifically for bath, and comprising compounds that are incompatible with each other that form layers when at rest imparting a different aspect to the cosmetic product are known from the prior art. Most of those known products contain at least one oily portion and an aqueous portion in addition to at least one surfactant compound.

Compositions consisting of two or more types of oil that are not compatible, or combinations of water/oil/alcohol, each component being incompatible with each other, or even emulsion-type compositions with one aqueous phase and one layer of alcohol are also known. Those compositions layers are mixed by a stirring step carried out by the end user at the moment of using the product.

Document EP0882442 (Shiseido) teaches a light-texture multi-layer composition that discloses the presence of a surfactant as an essential component which is the compound that supplies the main technical effect of the invention, that is to say, the effect of lightness of the product.

The so-called lightness of the product or a light-texture product related to cosmetic compositions, more specifically the compositions used during or after the bath, may be understood as being the ease of removing the product from the skin, as for instance, when the product is washed away by the water.

This characteristic is not always desired by the user since there are those who prefer products that leave behind on the skin a residual film that gives them a feeling of softness, hydration and brightness.

Document JP 4290810 teaches a composition having three layers: an oily layer, a surfactant layer comprising 1 or more types of surfactants, and an aqueous layer. That composition is described as having a transparent appearance and good emulsification when stirred. After remaining at rest for some time, separation of the phases occurs.

Since a considerable amount of surfactant is used, that product may cause problems on the skin. Moreover, when it is formulated as a product for bath, the conditions of mixture are not good, forming the so-called "oil droplets", causing an unpleasant feeling.

Document JP 10 1040413 (Max Fuakutac KK) describes the obtention of a 2-phase composition having one or more surfactants, and documents JP 63165304, JP 63165305, JP 63083009, JP 63083010, JP 63083011, JP 63033316 and JP 63033317 (Kanebo), disclose multilayer compositions in which a high percentage of surfactants is used, based on the total weight of the composition.

The surfactants belong to a class of raw materials that are known as primary irritants. Moreover, they interfere with the layers separation time, rendering the formation of the layers slower.

Another effect provided by the surfactant when mixed to a cosmetic composition is that it promotes the emulsification of the product, imparting a milky aspect when it is used in bathtubs or when applied to the body, which may be an undesirable effect for the end user.

The use of a surfactant emollient compound provides the solubilization of essential oils and their migration to the intermediate phase, which may nullify the essence that must be in the oily phase. This type of compound is generally used in cosmetic compositions in which the expected effect is that of a composition with a light formulation.

Another type of cosmetic composition that has two layers is the so-called biphasic composition, that is to say, with at least one lower phase and one upper phase which are designed for removing make-up.

Another drawback which the inventor has noticed in the known multilayer cosmetic compositions is that the use of dyes in a surfactant system is difficult to stabilize. They precipitate and migrate to other layers of the composition.

SUMMARY OF THE INVENTION

In order to eliminate the above-cited drawbacks, a multiphase cosmetic composition has been developed comprising at least one oily phase and at least one aqueous phase, wherein the composition further comprising a polyol, the oily phase comprising a mixture of at least one mineral oil and at least one vegetable oil, and the aqueous phase comprising a water-soluble salt.

The composition described above may be used in any cosmetic formulation, being more specifically a multi-phase cosmetic composition used during and/or after the bath and comprising a mixture of oils, a polyol and an aqueous phase with a pH that comes close to the human skin pH.

The composition of the invention shows two or more liquid, transparent and colorful layers when at rest, said layers becoming a homogeneous mixture when stirred. The phases or layers separation occurs more rapidly because the composition does not contain a surfactant. Moreover, since it does not contain such a compound, it does not irritate the skin and provides an improved "sensation" after use as the product leaves a residue on the skin that provides a feeling of softness and brightness apart from perfuming the skin.

DETAILS DESCRIPTION OF THE INVENTION

According to the present invention a composition is provided which comprises a mixture of oils that may be of mineral, vegetable and synthetic sources, an aqueous layer and at least one polyol.

Said oily layer comprises a mixture of mineral oil and vegetable oil, such as an oil selected from passion-fruit (or maracock) oil, Brazil-nut oil, cashew-nut oil, Brazilian wine-palm oil, and is present in a range of from 10 to 60%, more preferably from 25 to 50%, and stll more preferably fom 30 to 35%, by weight, based on the total weight of the composition.

Vegetable oils such as passion-fruit (or maracock) oil and Brazilian wine-palm oil are useful due to their rich composition of fatty acids that help in maintaining a thin protective layer on the skin.

The composition of the invention comprises, in a second layer, at least one polyol that may be selected from the group of alcohols, as for example, ethylene glycol, propylene glycol, hexylene glycol, sorbitol, diethylene glycol, polyethylene glycol, preferably hexylene glycol, which is present in a range of 25 to 50% by weight, more preferably from 30 to 35% by weight, based on the total weight of the composition.

For the formation of the layers, that is to say, for the separation of the composition into layers, water-soluble salts are used. The salts are used in a determined concentration range since they are soluble when use in a low concentration, and in this case separation of the composition into layers does not take place, while when they are used in high concentrations precipitation occurs.

According to the composition of the present invention the water-soluble salts are alkali metals and alkali earth metals salts such as sodium chloride, potassium chloride, magnesium chloride, sodium sulfate, magnesium sulfate, preferably sodium chloride, preferably employed at about 8 to 18% by weight, more preferably from 13 to 16% by weight, based on the total weight of the composition.

Other usual ingredients of cosmetic formulations are used herein, such as fragrances, preservatives, dyes, emollients, etc. Examples of essences that may be used include extracts from cocoa-nut and green malt.

The illustrative examples presented below serve for a better description of the invention. However, the data and procedures illustrated here merely refer to a few embodiments of the invention, and should not be taken as a limitation thereof.

EXAMPLE 1

A multilayer composition is prepared having first, second and third layers, which comprise:

First Layer:

| Ingredient | % |
|---|---|
| Glycerin | About 92 |
| Butylene glycol | 1-3 |
| methylparabene | 0.05-0.15 |
| propylparabene | 0.01-0.12 |
| Polyoxyethylene polyoxypropilene glycol | 0.03 |
| water | About 5 |
| EDTA tetrasodium | 0.5 |
| Sodium chloride | 0.5-1 |

Second Layer

| Ingredient | % |
|---|---|
| Ethoxilated glyceryl cocoate | 100 |

Third Layer

| Ingredient | % |
|---|---|
| Mineral oil | About 77 |
| Brazilian Wine-palm oil | 0.1-0.5 |
| Isopropyl palmitate | About 20 |
| Essence | 1-3 |
| Irgasan | 0.05 |
| BHT | 0.1 |

EXAMPLE II:

A mutilayer composition is prepared having first, second and third layers, which comprise:

First Layer

| Ingredient | % |
|---|---|
| Glycerin | About 92 |
| Butylene glycol | 1-3 |
| methylparabene | 0.05-0.15 |
| propylparabene | 0.01-0.15 |
| Polyoxyethylene polyoxypropilene | 0.03 |
| water | About 5 |
| EDTA tetrasodium | 0.2 |
| Sodium chloride | 0.75 |
| dyes | 0.92 |

Second Layer

| Ingredient | % |
|---|---|
| Dimeticone copolyol | 100 |

Third Layer

| Ingredient | % |
|---|---|
| Mineral oil | About 88 |
| Brazil-nut oil | 1.0-1.5 |
| Cashew-nut oil | 1.0-1.5 |
| Essence | 7.5-8.5 |
| Triclosan | 0.05 |
| BHT | 0.1 |

EXAMPLE III

A multilayer composition is prepared having first, second and third layers, which comprise:

First Layer

| Ingredient | % |
|---|---|
| water | About 83 |
| EDTA | 0.2 |
| Sodium chloride | About 16 |
| 2-bromo-2-nitropropane-1,3-diol | 0.1 |
| Sodium hydroxide | 0.005 |
| Dyes | 0.65 |

Second Layer

| Ingredient | % |
|---|---|
| Hexyleneglycol | 95-98 |
| Dyes | 2-5 |

Third Phase

| Ingredient | % |
|---|---|
| Mineral oil | About 77 |
| Isoparaffin | 20 |
| Essence | 1-3 |
| Triclosan | 0.05 |
| BHT | 0.1 |

EXAMPLE IV

A multilayer composition is prepared having first, second and third layers, which comprise:

First Layer

| Ingredient | % |
|---|---|
| Demineralized water | About 100 |
| EDTA disodium | 0.2 |
| Methylparabene | 0.001-0.003 |
| Sodium chloride | 10-15 |
| Sorbitol | 0.15-0.20 |
| Dyes | 1.65 |
| 2-bromo-2-nitropropane-1,3-diol | 0.1 |
| Sodium hydroxide | 0.005 |

Second Layer

| Ingredient | % |
|---|---|
| Hexylene glycol | About 99 |
| Ethyl alcohol | 0.048 |
| metylparabene | 0.003 |
| Dyes | 0.0007 |
| Demineralized water | Balance to 100 |

Third Layer

| Ingredient | % |
|---|---|
| Mineral oil | About 90 |
| Passion-fruit (or Maracok) oil | 0.5-1.5 |
| Essence | 7.5-9.0 |
| Triclosan | 0.05 |
| BHT | 1.0 |

EXAMPLE V

A multilayer composition is prepared having first, second and third layers, which comprise:

First Layer

| Ingredient | % |
|---|---|
| Demineralized water | About 100 |
| EDTA disodium | 0.2 |
| Methylparabene | 0.001-0.003 |
| Ethyl alcohol | 0.04 |
| Sodium chloride | 10-15 |
| Sorbitol | 0.15-0.20 |
| Dye | About 0.0045 |
| 2-bromo-2-nitropropan-1,3-diol | 0.1 |
| Sodium hydroxide | 0.005 |

Second Layer

| Ingredient | % |
|---|---|
| Hexylene glycol | About 97 |
| Ethyl alcohol | 0.10 |
| methylparabene | About 0.007 |
| Dyes | 0.0034 |
| Demineralized water | Balance to 100 |

Third Layer

| Ingredient | % |
|---|---|
| Mineral oil | About 93 |
| Brazilian Wine-palm oil | 0.5-1.5 |
| Essence | 6.0-7.5 |
| Triclosan | 0.05 |
| BHT | 1.0 |

Allergic Sensitivity Tests

For the research on the allergic sensitivity, the following clinical tests were carried out with the composition of Example IV: primary and accumulated skin irritability, skin sensitization, phototoxicity and photoallergy.

The researches employed the "patch test", which is the main tool used in diagnosing the reaction caused by a cosmetic formulation and in allergic sensitivity searches. The main potential risks of using a new product are primary irritation, allergy due to sensitization, phototoxicity and photoallergy. The tests consist repeatedly to apply the product to the skin and has the objective of detecting possible irritation or inducing sensitization (KLIG-MAN & WOODINGS, 1967, FISCHER 1978).

The research on primary skin irritability was carried out with 1200. volunteers of both sexes (103 women and 17 men), the ages ranging from 18 to 60 years, and the "patch test" was removed by the researchers after 48 hours of contact with the skin and the reactions ware written down 30 minutes after removal.

Result achieved: no volunteer presented any kind of reaction in the tested area.

The research on accumulated sensitization was carried out with 50 volunteers of both sexes (44 women and 06 men), the ages ranging from 18 to 40 years, with the applications being made every day, always in the same region and the contact test device remaining 72 hours in the weekend, during 4 consecutive weeks, in a total of 20 applications. After an interval of rest of 10 days, a simple patch was applied to the volunteers at a place where no patch had been applied before. Those contact tests were moved after 48 hours of contact with the skin and possible reactions were checked 30 minutes after withdrawal.

Result obtained: no volunteer presented any kind of reaction in the tested area.

The research on skin sensitization was made with 45 volunteers of both sexes (35 women and 10 men), their ages ranging from 18 to 60 years, with the applications being effected 3 times a week for 3 consecutive weeks in a total of 09 applications. All the contact tests devices were removed by the volunteers at home 24 hours after initiation of the test. After a period of rest of 10 days, a simple patch was applied to the volunteers at a place where no patch had been applied before. Those contact tests devices were removed after 48 hours of contact with the skin, and possible reactions were checked 30 minutes after withdrawal.

Result achieved: no volunteer presented any kind of reaction in the tested area.

The research on phototoxicity and photoallergy was carried out with 25 volunteers of both sexes (24 women and 1 man), their ages ranging from 19 to 48 years with the applications being made twice a week for 3 weeks in a total of 06 applications, always in the same region (right or left back). Every 24 hours, the contact tests devices were removed and the test areas were evaluated. Immediately after removal of the paches, the areas were irradiated with A and B ultraviolet lamps. The non-irradiated areas of the back were protected against the incidence of light. The samples were always reapplied to the same place. After the 6 consecutive applications and irradiations (induction), there is a period of 10 days in which no patch was applied and not irradiation was made.

Then, a patch was applied to a place where no patch had been applied before and those tests devices were removed after 48 hours of application. After removal, the tested areas were irradiated with UVA/UVB lamp. All volunteers were instructed to protect the skin irradiated area from sunlight. Evaluations were made 24 and 48 yours after the last irradiation and written down.

Result achieved: no volunteer presented any kind of reaction in the tested area.

The invention claimed is:

1. A multilayer cosmetic composition comprising at least one oily phase and at least one aqueous phase, characterized in that it comprises a polyol, that the oily phase comprises a mixture of at least one mineral oil and at least one vegetable oil, and that the aqueous phase comprises a water-soluble salt, and wherein the composition does not include a surfactant, and wherein the polyol is used at a concentration ranging from 25 to 50% by weight, based on the total weight of the composition.

2. A composition according to claim 1, characterized in that the oily layer that contains the mixture of mineral and vegetable oils comprises from 10 to 60%, by weight, of the total weight of the composition.

3. A composition according to claim 2, characterized in that the oily layer that contains the mixture of mineral and vegetable oils comprises from 25 to 50% by weight, of the total weight of the composition.

4. A composition according to claim 3, characterized in that the oily layer that contains the mixture of mineral and vegetable oils comprises from 30 to 35% by weight, of the total weight of the composition.

5. A composition according to claim 1, characterized in that the polyol is used at a concentration ranging from 30 to 35% by weight, based on the total weight of the composition.

6. A multilayer cosmetic composition comprising at least one oily phase and at least one aqueous phase, characterized in that it comprises a polyol, that the oily phase comprises a mixture of at least one mineral oil and at least one vegetable oil, and that the aqueous phase comprises a water-soluble salt, and wherein the composition does not include a surfactant, and wherein the water-soluble salt is present at a concentration ranging from 8 to 18% by weight, based on the total weight of the composition.

7. A composition according to claim 6, characterized in that the water-soluble salt is present at a concentration ranging from 13 to 16% by weight, based on the total weight of the composition.

8. A composition according to claim 1, characterized in that the vegetable oil is selected from the group consisting of passion-fruit oil, Brazil-nut oil, cashew-nut oil, Brazilian wine-palm oil and mixtures thereof.

9. A composition according to claim 1, characterized in that the polyol is selected from alcohols comprising ethylene glycol, propylene glycol, hexylene glycol, sorbitol, diethylene glycol, polyethylene glycol and mixtures thereof.

10. A composition according to claim 9, characterized in that the polyol is hexylene glycol.

11. A composition according to claim 1, characterized in that the water-soluble salts are selected from the group consisting of alkaline metal and alkaline earth metal salts.

* * * * *

UNITED STATES PATENT AND TRADEMARK OFFICE
CERTIFICATE OF CORRECTION

PATENT NO.        : 7,988,981 B2
APPLICATION NO.   : 10/510845
DATED             : August 2, 2011
INVENTOR(S)       : Di Puccio Pagano It is certified that error appears in the above-identified patent and that said Letters Patent is hereby corrected as shown below:

Column 2,
Line 45, "and stll more preferably fom 30" should read --and still more preferably from 30--.

Signed and Sealed this
Sixteenth Day of October, 2012

David J. Kappos
*Director of the United States Patent and Trademark Office*